(12) United States Patent
Manique et al.

(10) Patent No.: US 6,566,490 B1
(45) Date of Patent: May 20, 2003

(54) SEEDING CRYSTALS FOR THE PREPARATION OF PEPTIDES OR PROTEINS

(75) Inventors: Flemming Manique, Ballerup (DK); Christian Ilsoe, Vaerlose (DK)

(73) Assignee: Novo Nordisk A/S, Bagsvaerd (DK)

( * ) Notice: Subject to any disclaimer, the term of this patent is extended or adjusted under 35 U.S.C. 154(b) by 25 days.

(21) Appl. No.: 09/742,193

(22) Filed: Dec. 20, 2000

Related U.S. Application Data

(63) Continuation of application No. PCT/DK99/00371, filed on Jun. 30, 1999, said application No. 60/092,882, filed on Jul. 15, 1998.

(30) Foreign Application Priority Data

Jun. 30, 1998 (EP) ............................................. 98610020

(51) Int. Cl.[7] ........................... C07K 14/62; C30B 29/58
(52) U.S. Cl. ..................... 530/304; 530/305; 530/308; 530/344; 530/399; 530/412; 530/418; 530/427; 23/301
(58) Field of Search ............................... 23/301; 514/3, 514/4, 12, 21; 530/300, 303, 304, 305, 308, 324, 344, 345, 350, 397, 398, 399, 412, 417, 418, 427

(56) References Cited

U.S. PATENT DOCUMENTS 5,504,188 A 4/1996 Baker et al. ................. 530/304

FOREIGN PATENT DOCUMENTS

| EP | 0 096 631 A1 | 12/1983 |
|----|--------------|---------|
| EP | 0 582 351 A1 | 2/1994 |
| GB | 766994 | 1/1957 |
| GB | 766995 | 1/1957 |
| WO | WO 88/02633 | 4/1988 |
| WO | WO 90/00176 | 1/1990 |

OTHER PUBLICATIONS

Luft et al. A method to produce microseed stock . . . Acta Crystallographica Section D. May 1999, vol. 55, No. 5, pp. 988–993.*

DeMattei et al., Journal of Crystal Growth, vol. 122, pp. 21–30 (1992).

Abstract of Japanese Patent Application No. 04–288013 (Oct. 13, 1992).

* cited by examiner

Primary Examiner—Jeffrey E. Russel
(74) Attorney, Agent, or Firm—Reza Green

(57) ABSTRACT

Disclosed is a method for producing seeding microcrystals for the production of human insulin, the microcrystals being free of non-human pancreatic insulin, the method comprising providing an unseeded suspension of human insulin, the suspension being free of non-human pancreatic insulin, and homogenizing the insulin suspension under pressure to result in human insulin microcrystals suitable for use as seeding microcrystals for the production of zinc insulin products. The method of homogenization under pressure may also be used for the production of seeding mnicrocrystals for other peptides and proteins, in particular pharmaceutical peptides or proteins such as insulin, GLP-1, glucagon and growth hormones.

11 Claims, 1 Drawing Sheet

SEEDING CRYSTALS FOR THE PREPARATION OF PEPTIDES OR PROTEINS

CROSS-REFERENCE TO RELATED APPLICATIONS

This application is a continuation of PCT/DK99/00371, with an international filing date of Jun. 30 1999, published in English under PCT Article 21(2); and claims benefit under 35 U.S.C. 120 of PCT/DK99/00371, which claims priority of EP 98/610020, filed Jun. 30 1998, and U.S. provisional application No. 60/092,882, filed Jul. 15 1998, the contents of which are hereby incorporated by reference in their entirety.

FIELD OF THE INVENTION

The present invention relates to seeding crystals for the preparation of peptides or proteins such as zinc insulin products.

BACKGROUND OF THE INVENTION

The "Lente" family of zinc insulin products are insulin zinc suspensions of the type originally developed in the 1950's with the aim of producing insulin preparations that would be able to cover diabetics' insulin requirement with a single daily injection (see erg. Jens Brange, *Galenics of Insulin*, 1987). Various Lente insulin products having different action profiles are available in the form of different combinations of amorphous and/or crystalline insulin particles from Novo Nordisk A/S, Denmark These include SEMILENTE, a suspension of amorphous insulin particles, ULTRALENTE, a suspension of crystalline insulin particles, and LENTE, which is a mixture of 30% amorphous and 70% crystalline insulin particles.

For several decades, seeding crystals for preparation of the "Lente" zinc insulin products have been prepared by the same basic freeze-drying method that was developed and patented in the early 1950's. This method, which is described in GB patent specification No. 766,994, involves the addition of freeze-dried amorphous insulin, typically beef insulin, to an insulin-containing crystallization medium to result in the formation of a suspension of insulin microcrystals of a size of about 2–7 µm. This suspension, which is eventually used for the preparation of the final crystalline zinc insulin product, is filled into small vials (e.g. 10 ml), frozen in an alcohol/carbon dioxide mixture and stored frozen at a temperature at or below –18° C.

Although still in use, this method has a number of disadvantages:
1. It is based on the use of beef insulin, since it has until now not been possible to produce acceptable microcrystals of pure human insulin. As a result of the use of beef insulin nuclei for the formation of the microcrystals, the end product contains a small amount of beef insulin, which is undesirable.
2. The freeze-drying method requires a lyophilizer and subsequent shipping and storage at a temperature of no more than –18° C. This is expensive and requires a great deal of space.
3. The method of preparation is extremely difficult to perform in a sufficiently aseptic manner.

It would therefore be advantageous to be able to produce insulin seeding crystals using a method which does not suffer from the disadvantages of the known methods. It has now surprisingly been found that it is possible, using a relatively simple and inexpensive process, to produce insulin seeding crystals which are free of beef insulin, which can be stored at room temperature and which result in insulin preparations having advantageous properties in terms o,f e.g., crystal particle size and uniformity. Furthermore, it is also contemplated that this process will be applicable to the production of seeding crystals for other peptides and proteins, in particular peptides or proteins used as pharmaceuticals.

SUMMARY OF THE INVENTION

It is thus an object of the present invention to provide a novel method for the production of peptide or protein seeding crystals. More particularly, it is an object of the invention to provide a method for the production of insulin seeding crystals which does not require the use of beef insulin, which makes possible storage and transport without the need for expensive freeze-drying and storage at sub-zero temperatures, and which can be performed in a closed system so as to more readily allow the use of aseptic production methods.

Another object of the invention is to provide a method for the preparation of insulin seeding crystals for the production of crystalline zinc insulin suspensions having a narrow particle size distribution.

In its broadest aspect, the present invention thus relates to a method for producing seeding microcrystals for the production of a peptide or protein, comprising providing an unseeded suspension of a peptide or protein and homogenizing said suspension under pressure to result in peptide or protein microcrystals suitable for use as seeding microcrystals.

In a particular embodiment, the invention relates to a method for producing seeding microcrystals for the production of human insulin, said microcrystals being free of non-human pancreatic insulin, comprising providing an unseeded suspension of human insulin, said suspension being free of non-human pancreatic insulin, and homogenizing said insulin suspension under pressure to result in human insulin microcrystals suitable for use as seeding microcrystals for the production of zinc insulin products.

Another aspect of the invention relates to a method for the production of a peptide or protein product, comprising providing an unseeded suspension of a peptide or protein and seeding said suspension with microcrystals produced by the method indicated above.

In a particular embodiment of this aspect of the invention, the peptide or protein product to be produced is a zinc insulin product, and the unseeded suspension is a suspension of human insulin.

A further aspect of the invention relates to human insulin microcrystals suitable for use as seeding microcrystals for the production of zinc insulin products, said microcrystals being free of non-human pancreatic insulin.

A still further aspect of the invention relates to human zinc insulin product free of non-human pancreatic insulin.

DETAILED DESCRIPTION OF THE INVENTION

Figure 1:
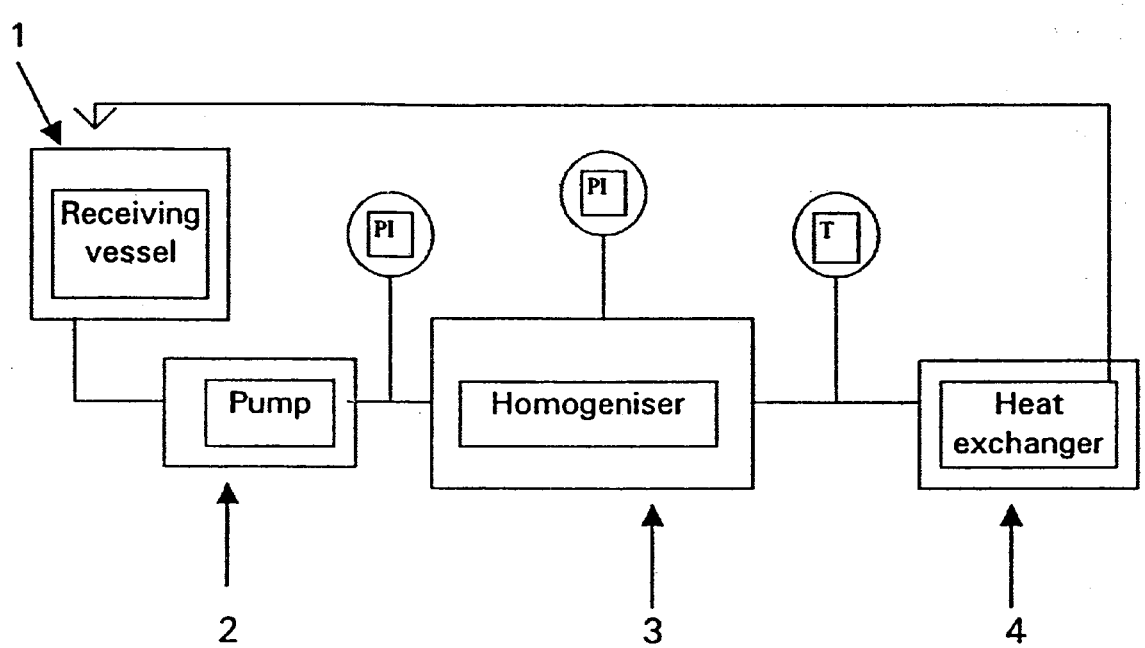
FIG. 1 is a schematic representation of a system for practicing the present invention.

As indicated above, the method of the invention is directed to the production of seeding microcrystals for peptides and proteins in general, in particular for peptides and proteins that are used as pharmaceuticals. More particularly, the method is directed to seeding microcrystals for the production of therapeutic peptides or proteins such as insulin, GLP-1, glucagon, and growth hormones such as human growth hormone, as well as analogues and derivatives of such peptides and proteins. The peptide or protein is in particular human insulin or an analogue or derivative thereof as described below. In the context of peptides and proteins other than insulin, the terms "analogue" and "derivative" are to be understood analogously to the definitions given below in the context of insulin.

As used in the present text, the term "human insulin" is used to designate naturally occurring human insulin as well as insulin analogues and insulin derivatives. The term "insulin analogue" is used to designate a peptide with insulin activity, derived from a naturally occurring insulin by substitution of one or more amino acid residues, deletion of one or more amino acid residues and/or addition of one or more amino acid residues. An insulin or insulin analogue may optionally be in the form of an "insulin derivative", the term "derivative" referring to a peptide in which one or more of the amino acid residues of the parent peptide have been chemically modified, e.g., by alkylation, acylation, ester formation or amide formation. An "acylated insulin" (or insulin analogue) is an insulin (or insulin analogue) which has an acyl group in the ε-amino group of one or more amino acid residues, often a lysine residue.

As used herein, the term "non-human pancreatic insulin" refers to naturally occurring insulin from a non-human source, e.g., bovine or porcine insulin.

The basic principle of a presently preferred embodiment of the invention is shown schematically in FIG. 1. The apparatus of FIG. 1 comprises a receiving vessel 1, from which the insulin suspension is transferred by means of a pump 2 into a homogenizer 3. The homogenizer 3 comprises a valve with a very small opening through which the insulin suspension is pumped at a high pressure, e.g., about 1000 bars or higher. Upon exiting the valve, the insulin suspension is subjected to a sudden drop in pressure, which results in the rupture of the insulin crystals, i.e., a homogenization effect. Since the insulin suspension is preferably subjected to multiple homogenization cycles in order to result in a sufficiently homogenous suspension of microcrystals having the desired particle size and size distribution, and since the high pressure used in the homogenizer 3 results in an increase in the temperature of the suspension, the apparatus preferably also comprises a heat exchanger 4 downstream of the homogenizer 3 in order to reduce the suspension temperature. From the heat exchanger 4, the insulin suspension is returned to the receiving vessel 1 for further homogenization cycles as necessary.

The temperature of the suspension increases according to the following equation:

$$\Delta T = P/(c \times \delta)$$

where:
ΔT=temperature increase (° C.)
P=suspension pressure (N×m$^{-2}$)
δ=suspension density (g×m$^{-3}$)
c=specific heat (J×g$^{-1}$×°C$^{-1}$)

The pressure and temperature are monitored during the process, and the above equation can be used in connection with design of the apparatus and regulation of the process.

In the method according to the invention, homogenization is typically performed at a pressure of at least about 500 bars, preferably at least about 800 bars, more preferably at least about 1000 bars. In certain cases, the pressure may, e.g., beat least about 1200 bars, for example up to about 1500 bars or more, even though such high pressures of above about 1000 bars are generally not believed to be necessary.

In a preferred embodiment, homogenization of the suspension is performed using multiple homogenization cycles, i.e., at least 2 cycles, since the use of multiple homogenization cycles has been found to provide improved results, i.e. optimisation of seeding crystal size and uniformity. It is thus contemplated that it will normally be advantageous to use more than 2 cycles, such as 3, 4, 5, 6, 7, 8, 9 or 10 cycles or even more, e.g., in certain cases up to 15 or 20 cycles or perhaps even more than 20 cycles. The most advantageous number of homogenization cycles will be determined by the person skilled in the art in each individual case based on factors such as the nature of the insulin suspension, the nature of the homogenization apparatus used, the pressure used for homogenization, and the desired insulin microcrystal particle size and size distribution.

Since, as indicated above, the high pressure used in the homogenizer results in an increase in the temperature of the suspension, the use of multiple homogenization cycles is preferably accompanied by the use of a heat exchanger in order to reduce the suspension temperature, so that the suspension is maintained at a suitable temperature throughout the homogenization process. Such heat exchangers are known in the art, and the person skilled in the art will readily be able to adapt the characteristics of the heat exchanger to suit the given process and apparatus. Preferably, the temperature of the recycled insulin suspension is maintained within the range of about 10–40° C., e.g., about 20–35° C.

Although the particle size of the resulting insulin microcrystals will vary depending on the intended use, suitable microcrystals will often have an average particle size, as defined by the longest diagonal of the crystals, in the range of about 0.5–4 μm, e.g., about 1–3 μm.

The result of the homogenization process is human insulin microcrystals suitable for use as seeding microcrystals for the production of zinc insulin products, the microcrystals having the important feature of being free of non-human pancreatic insulin. For the production of zinc insulin products, the seeding microcrystals of the invention will be used in a conventional manner, i.e., an unseeded suspension of human insulin is seeded with the suspension of microcrystals produced as described above, and crystallization is allowed to proceed in a manner known per se in the art. As is normal in the art, the precise amount of microcrystals to be added to a given unseeded insulin suspension may be determined empirically.

The invention will be further illustrated by the following non-limiting examples.

EXAMPLES

Materials and Methods

Using the basic homogenization process and apparatus described above, i.e., a recirculating homogenizer equipped with a heat exchanger, a number of experiments were performed to test the effect of the number of homogenization cycles as well as homogenization pressure and time.

The apparatus used was a Rannie high pressure homogenizer, model LAB 10,51 VH (series 1.89239), equipped with a ceramic valve, type SEO 719685. The capacity of the homogenizer was 80 l/h at a pressure of 1000 bars. A centrifugal pump provided an inlet pressure of 4.5–5 bars. The heat exchanger for these experiments used a cooling water temperature of about 20° C. However, since the capacity of the heat exchanger was insufficient in relation to this particular homogenizer, the outlet temperature of the insulin suspension was somewhat higher at the maximum homogenizer output, i.e., about 28–29° C., but slightly lower at a lower homogenizer output of about 65 l/h, i.e., about 24–28° C. The receiving vessel comprised a 100 l pressure tank and a small conic vessel with a volume of about 3 l.

The insulin suspension used for producing the microcrystals was a pooled batch (2×20 l) of unseeded ULTRALENTE HM(ge), 100 U/ml, from Novo Nordisk A/S.

Example 1

A 10 l portion of the pooled batch of the ULTRALENTE insulin suspension was homogenized at a pressure of 1000 bars, the suspension being recirculated for multiple homogenization cycles as described above, resulting in a gradually increased degree of homogenization. A flow rate of 80 l/h was used. A total of 18 homogenization cycles were performed, and samples were taken for the first 10 cycles and after the final cycle. The temperature of the insulin suspension was measured in the outlet conduit between the homogenizer and the heat exchanger. The times and measured temperatures for the various cycles were as indicated in Table 1 below:

TABLE 1

| Example number | Number of homogenization cycles | Time from start (minutes) | Temperature (° C.) |
|---|---|---|---|
| 1-0 | 0 | 0 | 12.5 |
| 1-1 | 1 | 5 | 29 |
| 1-2 | 2 | 12 | 29 |
| 1-3 | 3 | 19 | 28.3 |
| 1-4 | 4 | 26 | 29.5 |
| 1-5 | 5 | 33 | 29.5 |
| 1-6 | 6 | 40 | 29.8 |
| 1-7 | 7 | 47 | 29.5 |
| 1-8 | 8 | 54 | 29.2 |
| 1-9 | 9 | 61 | 28.1 |
| 1-18 | 18 | 122 | 28.1 |

A number of the samples were investigated by microscope, and the following observations were made:

Example 1-0: mostly whole and sharp-edged rhombohedric crystals having a size of about 3–80 μm; some broken crystals and crystal fragments.

Example 1-1: still many whole rhombohedric crystals having a size of about 20–40 μm, but also many small crystal fragments with a size of 3 μm or less.

Example 1-2: still some whole rhombohedric crystals with a size of up to about 20 μm as well as a few larger crystal agglomerations of up to about 40 μm; even more small crystal fragments of 3 μm or less.

Example 1-18: small microcrystals of about 1 μm or less; a few crystal fragments of up to about 10 μm; no whole rhombohedric crystals.

Example 2

A 5 l portion of the pooled batch of the ULTRALENTE insulin suspension was homogenized at a pressure of 1000 bars, the suspension being recirculated for multiple homogenization cycles as described above, using a flow rate of 65 l/h. A total of 10 homogenization cycles were performed, and samples were taken after each cycle. In this case, instead of being led directly back to the receiving vessel from the heat exchanger, the suspension was collected after each cycle. A sample was taken from each portion, and the remainder of the portion was returned to the receiving vessel for the next homogenization cycle. The times and measured temperatures were as follows:

TABLE 2

| Example number | Number of homogenization cycles | Time from start (minutes) | Temperature (° C.) |
|---|---|---|---|
| 2-0 | 0 | 0 | — |
| 2-1 | 1 | — | 24.5 |
| 2-2 | 2 | — | 26.3 |
| 2-3 | 3 | — | 27.1 |
| 2-4 | 4 | 15 | 27.7 |
| 2-5 | 5 | — | 27.8 |
| 2-6 | 6 | — | 28.0 |
| 2-7 | 7 | — | 28.0 |
| 2-8 | 8 | — | 28.0 |
| 2-9 | 9 | — | — |
| 2-10 | 10 | 30 | — |

Example 3

In order to investigate the effect of the homogenization pressure, tests were performed at 1400–1500 bars, with a total of 9 homogenization cycles. Due to the increased pressure and the accompanying increased temperature of the suspension, the flow rate was further reduced to 54 l/h to allow the heat exchanger to provide a sufficiently reduced temperature. The batch size in this case was 3 l. The temperature of the suspension was maintained at about 26–29° C.

TABLE 3

| Example number | Number of homogenization cycles | Time from start (minutes) | Temperature (° C.) |
|---|---|---|---|
| 3-0 | 0 | 0 | 16.3 |
| 3-9 | 9 | 30 | 28.6 |

Example 4

The same procedure as in Example 3 was used, with the exception that the ULTRALENTE insulin suspension in this case had formed divergent crystals ("roses") during crystallization. The batch size was 2 l, and the homogenization time was therefore reduced correspondingly to a total of 21 minutes.

TABLE 4

| Example number | Number of homogenization cycles | Time from start (minutes) | Temperature (° C.) |
|---|---|---|---|
| 4-0 | 0 | 0 | — |
| 4-9 | 9 | 21 | 27.7 |

Example 5

Seeding Experiments With Selected Batches of Microcrystals

Seeding experiments were performed to test selected batches of the human insulin microcrystals prepared as described above. As a reference, a standard bovine microcrystal seeding batch was also tested. These experiments were performed using 1 l batches of ULTRALENTE (40 U/ml). Crystallization was performed using propeller agitation for a period of 20 hours. The results are shown in Table 5 below.

TABLE 5

| Microcrystals of Example number | Average crystal size (µm) | 10%–90% Deviation (µm) |
|---|---|---|
| Reference | 28 | 16 |
| 1-18 | 23 | 15 |
| 2-10 | 26 | 17 |
| 3-9 | 26 | 17 |
| 4-9 | 27 | 16 |

It may be seen from the results in Table 5 that the human insulin microcrystals prepared according to the invention gave an insulin crystal size and deviation comparable to that obtained using the standard bovine microcrystals, and that the five seeding batches gave largely identical results.

The five insulin batches prepared as described above were in addition analyzed with regard to a number of other parameters, including pH, insulin strength, A+M+B component, percentage of amorphous insulin, content of methyl para-hydroxybenzoate, dimer and polymer content, acidic and neutral desamidoins, content, and zinc content. It was found that insulin batches prepared using microcrystals according to the invention were generally comparable to insulin prepared using the standard bovine microcrystals.

Since it is known that the crystallization time and type of agitation can have an effect on the appearance of the rhombohedrons that are formed, a single batch prepared according to the invention (Example 3-9) was used for seeding tests in which the crystallization time and type of agitation were varied. With regard to agitation, no substantial differences were observed between crystals obtained using propeller agitation and agitation using "cradle movements". With regard to crystallization time, it was found that 4 hours was sufficient, i.e., a crystallization time of 20 hours was found to be unnecessary. There was a tendency for the best results to be obtained using propeller agitation and a crystallization time of 4 hours, as this led to the least amount of deviating crystals.

Conclusion

It may be concluded that pure microcrystals of human insulin can be produced by high pressure homogenization of an unseeded ULTRALENTE HM(ge) preparation. This method results in microcrystals in the form of small crystal fragments with a particle size of about 1–2 µm and some larger fragments with a particle size of up to about 10 µm.

Varying the pressure from 1000 bars to about 1500 bars did not have any noticeable effect on the microcrystals. On the other hand, the number of homogenization cycles has an effect, at least up to a point, an increased number of cycles resulting in a more uniform microcrystal suspension with a larger proportion of microcrystals having a size of about 1–2 µm and a smaller proportion of larger crystal fragments and whole rhombohedric crystals.

However, the number of homogenization cycles required to result in a given degree of homogenization is also related to the homogenization time per cycle.

The increase in temperature of the suspension measured in these experiments as a result of the homogenization process did not appear to affect the microcrystals in terms of chemical degradation. Temperature regulation can be optimized by suitable changes in e.g., the design and capacity of the heat exchanger.

The variation in the particle size of the microcrystals produced in these tests, and thus the variation in particle size of the zinc insulin product prepared using the microcrystals, could, if desired or necessary, be reduced by means of, e.g., sedimentation or centrifugation.

The seeding qualities of the microcrystals produced according to the invention have been shown to be acceptable, since the microcrystals result in zinc insulin products with rhombohedric crystals having an acceptable crystal size.

What is claimed is:

1. A method for producing seeding microcrystals for the production of a peptide or protein, comprising: providing an unseeded suspension of a peptide or protein and homogenizing said suspension under pressure to result in peptide or protein microcrystals suitable for use as seeding microcrystals for the production of said peptide or protein.

2. The method of claim 1, wherein the peptide or protein is a pharmaceutical peptide or protein.

3. The method of claim 2, wherein the peptide or protein is selected from the group consisting of insulin, GLP-1, glucagon, and growth hormones, as well as analogues and derivatives thereof.

4. The method of claim 1 for producing seeding microcrystals for the production of human insulin, said microcrystals being free of non-human pancreatic insulin, comprising: providing an unseeded suspension of human insulin, said suspension being free of non-human pancreatic insulin, and homogenizing said insulin suspension under pressure to result in human insulin microcrystals suitable for use as seeding microcrystals for the production of zinc insulin products.

5. The method of claim 1, wherein homogenization is performed at a pressure of at least about 500 bars.

6. The method of claim 1, wherein homogenization is performed using multiple homogenization cycles.

7. The method of claim 6, wherein the temperature of the suspension during said homogenizing step is controlled using a heat exchanger.

8. The method of claim 7, wherein the temperature of the suspension during said homogenizing step is maintained within the range of about 10–40° C.

9. The method of claim 1, wherein the microcrystals have an average particle size, as defined by the longest diagonal of the crystals, in the range of about 0.5–4 µm.

10. A method for the production of a peptide or protein product, said method comprising: (i) providing a first unseeded suspension of a peptide or protein; (ii) homogenizing said unseeded suspension under pressure to result in microcrystals of said peptide or protein; and (iii) seeding a second unseeded suspension of said peptide or protein with microcrystals produced in step ii.

11. The method of claim 10, wherein the peptide or protein product to be produced is a zinc insulin product, the first and second unseeded suspensions are suspensions of human insulin, and the seeding microcrystals are human insulin microcrystals.

* * * * *